(12) United States Patent
Biedermann et al.

(10) Patent No.: US 9,956,012 B2
(45) Date of Patent: May 1, 2018

(54) EXTENSION DEVICE FOR A BONE ANCHOR, IN PARTICULAR FOR MINIMALLY INVASIVE SURGERY

(71) Applicant: Biedermann Technologies GmbH & Co. KG, Donaueschingen (DE)

(72) Inventors: Timo Biedermann, Trossingen (DE); Berthold Dannecker, St. Georgen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 98 days.

(21) Appl. No.: 14/740,228

(22) Filed: Jun. 15, 2015

(65) Prior Publication Data

US 2015/0359571 A1 Dec. 17, 2015

Related U.S. Application Data

(60) Provisional application No. 62/013,421, filed on Jun. 17, 2014.

(30) Foreign Application Priority Data

Jun. 17, 2014 (EP) ..................................... 14172835

(51) Int. Cl.
*A61B 17/70* (2006.01)
(52) U.S. Cl.
CPC ........ *A61B 17/7076* (2013.01); *A61B 17/708* (2013.01); *A61B 17/7032* (2013.01)
(58) Field of Classification Search
CPC .................................. A61B 17/7076–17/7082
See application file for complete search history.

(56) References Cited

U.S. PATENT DOCUMENTS 7,563,264 B2    7/2009   Landry et al.
8,439,922 B1 *   5/2013   Arnold ............... A61B 17/7082
                                                     606/104

(Continued)

FOREIGN PATENT DOCUMENTS

WO   WO 2013/112689 A2   8/2013
WO   WO 2013/187928 A1   12/2013

OTHER PUBLICATIONS

European Search Report; Application Serial No. 14172835.2; dated Jan. 29, 2015; 13 sheets.

*Primary Examiner* — Jacqueline Johanas
(74) *Attorney, Agent, or Firm* — Lewis Roca Rothgerber Christie LLP

(57) ABSTRACT

An extension device for a bone anchor is provided, where the bone anchor includes an anchoring section and a receiving part connected to the anchoring section having a central axis. The extension device includes a first sleeve with a first sleeve axis that is coaxial to the central axis of the receiving part and is configured to be coupled to and decoupled from the receiving part. The extension device further includes a second sleeve with a second sleeve axis coaxial to the central axis. The second sleeve is positioned within the first sleeve, is positionable relative to the first sleeve along the central axis, and is configured to be coupled to and decoupled from the receiving part. The extension device also includes a locking member that, in a first configuration, inhibits decoupling of the first sleeve or the second sleeve from the receiving part when the other one of the first sleeve or the second sleeve is coupled to the receiving part.

26 Claims, 10 Drawing Sheets

(56) References Cited

U.S. PATENT DOCUMENTS

| | | |
|---|---|---|
| 2005/0131408 A1 | 6/2005 | Sivcol et al. |
| 2006/0200132 A1* | 9/2006 | Chao .................... A61B 17/708 |
| | | 606/86 A |
| 2008/0077134 A1* | 3/2008 | Dziedzic ............ A61B 17/8875 |
| | | 606/86 A |
| 2008/0125788 A1 | 5/2008 | Cohen et al. |
| 2008/0172062 A1* | 7/2008 | Donahue .............. A61B 17/708 |
| | | 606/104 |
| 2011/0313477 A1* | 12/2011 | McLean ............. A61B 17/7032 |
| | | 606/86 A |
| 2012/0253402 A1* | 10/2012 | McLean ............. A61B 17/7032 |
| | | 606/264 |
| 2014/0039567 A1 | 2/2014 | Hoefer et al. |
| 2014/0052187 A1 | 2/2014 | McBride et al. |
| 2014/0163625 A1* | 6/2014 | Meyer ................ A61B 17/7086 |
| | | 606/86 A |
| 2014/0277137 A1* | 9/2014 | Stad ................... A61B 17/7076 |
| | | 606/246 |

* cited by examiner

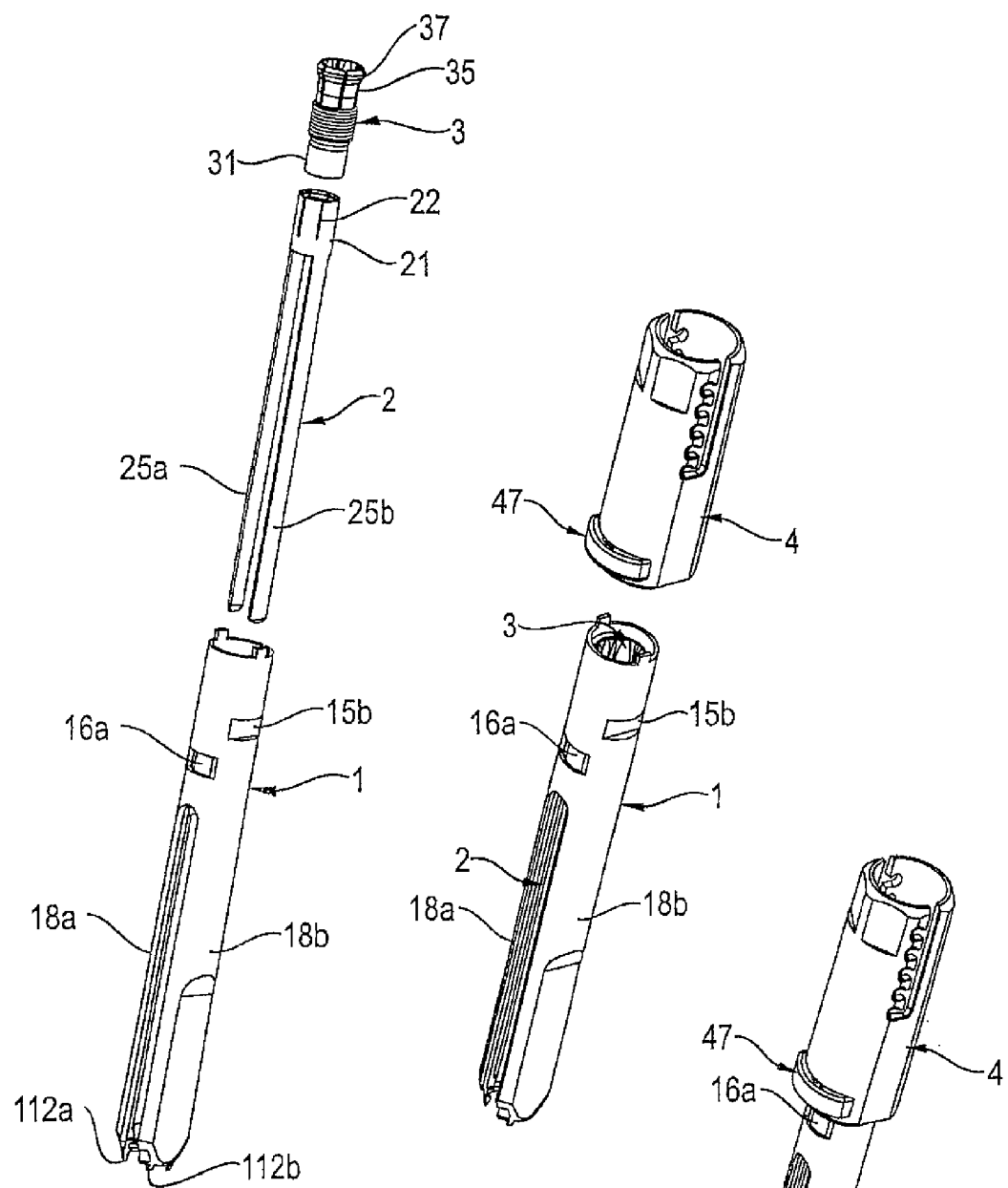

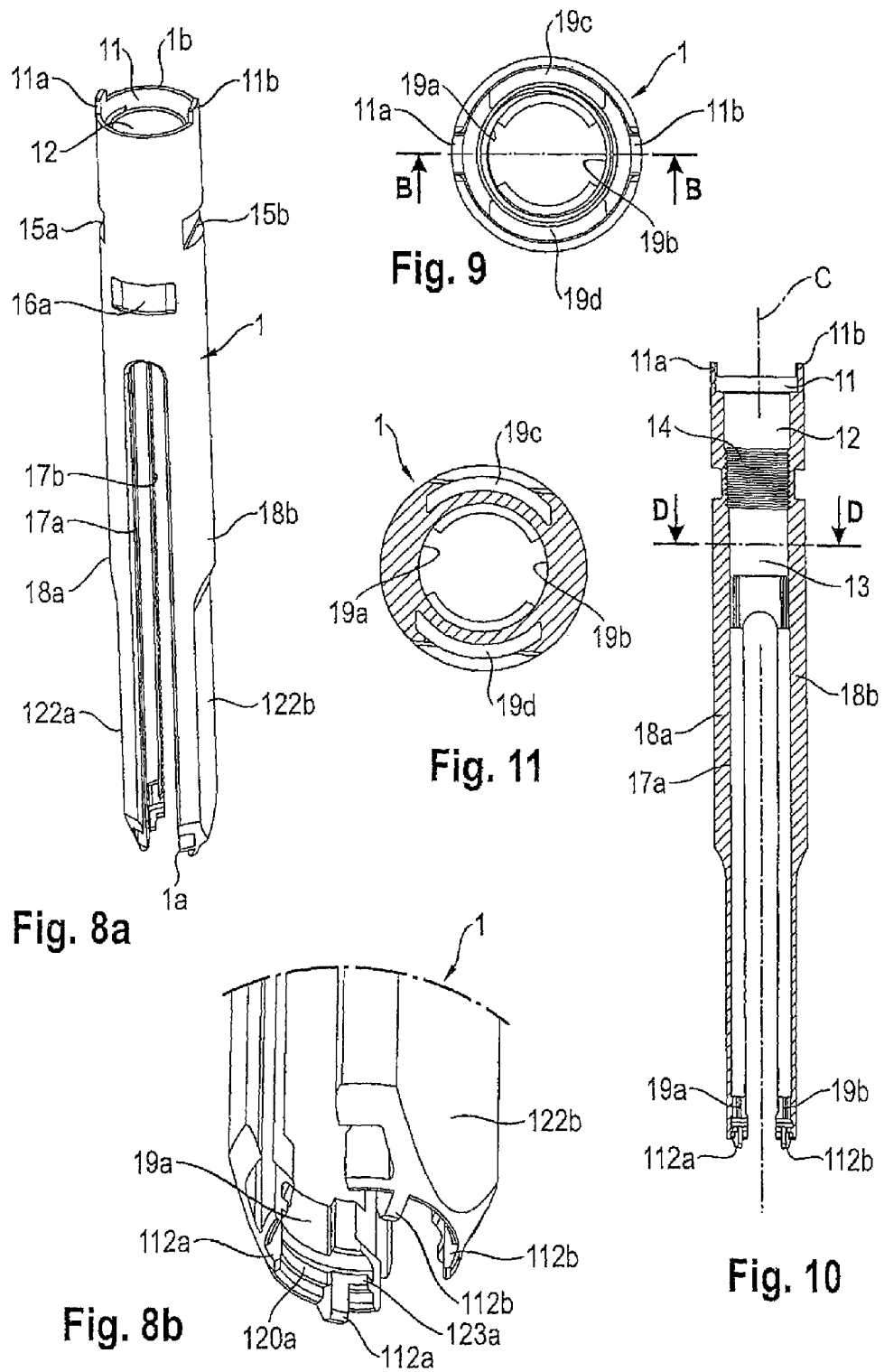

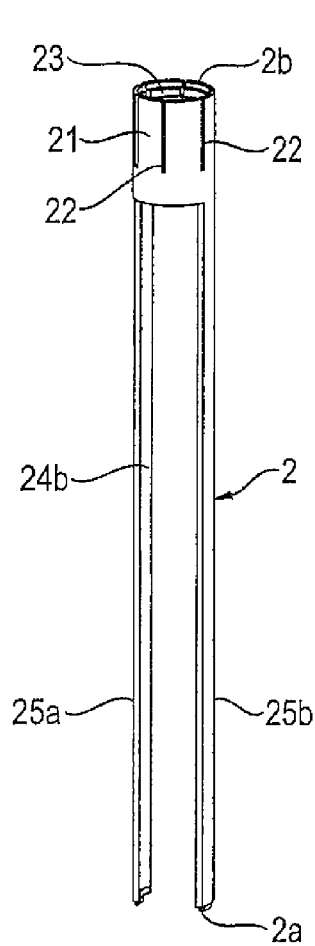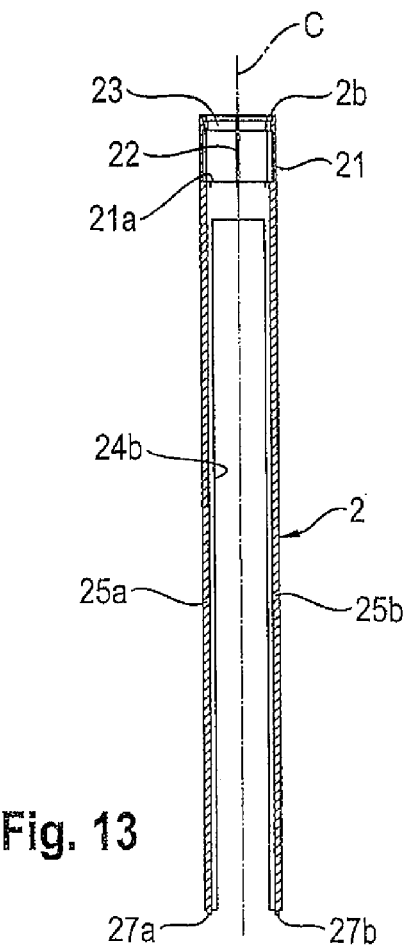
Fig. 12a
Fig. 13
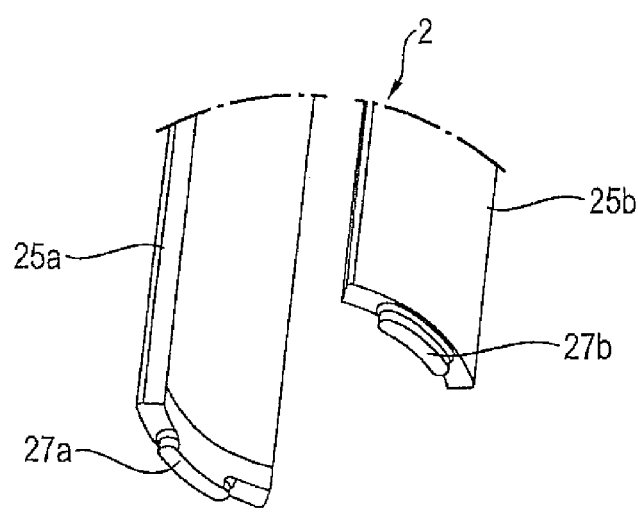
Fig. 12b

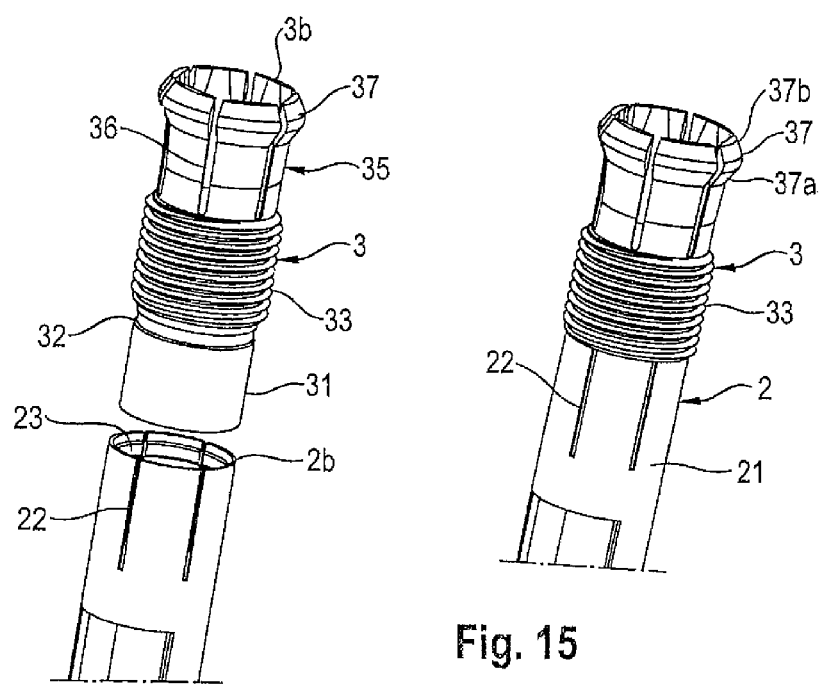
Fig. 14
Fig. 15
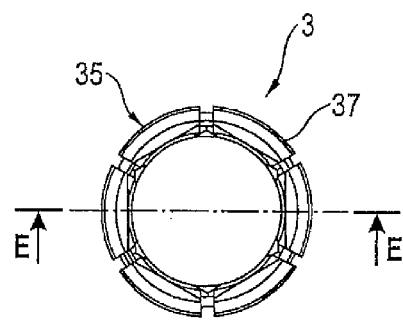
Fig. 16
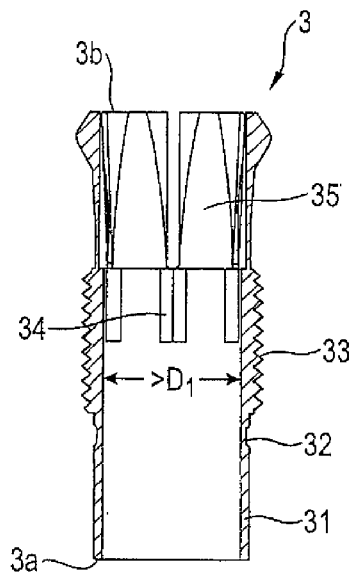
Fig. 17

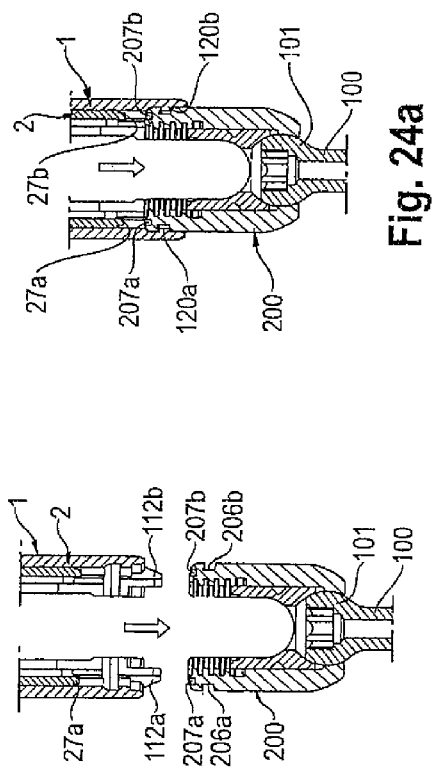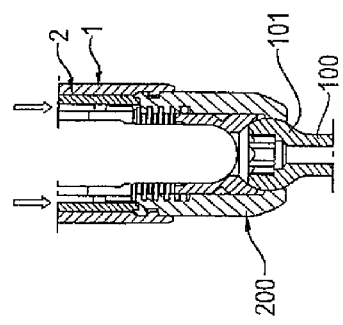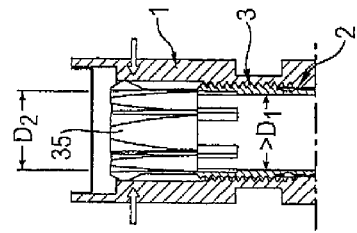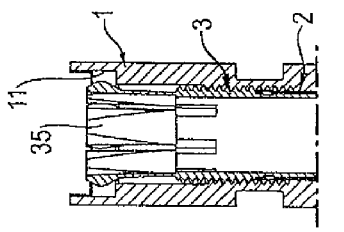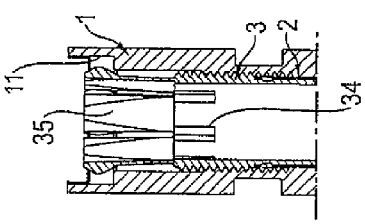

EXTENSION DEVICE FOR A BONE ANCHOR, IN PARTICULAR FOR MINIMALLY INVASIVE SURGERY

CROSS-REFERENCE TO RELATED APPLICATIONS

The present disclosure claims the benefit of U.S. Provisional Patent Application Ser. No. 62/013,421, filed on Jun. 17, 2014, the contents of which are hereby incorporated by reference in their entirety, and claims priority to European Patent Application EP 14172835.2, filed on Jun. 17, 2014, the contents of which are hereby incorporated by reference in their entirety.

BACKGROUND

Field

The present disclosure relates to an extension device for a bone anchor, in particular for use in minimally invasive surgery (MIS). The present disclosure also relates to a system including such an extension device and a bone anchor, where the bone anchor includes an anchoring section and a receiving part for receiving a rod to couple the rod to the anchoring section. The extension device includes a first sleeve and a second sleeve that are each configured to be coupled to the receiving part such that translational and rotational movement of the extension device relative to the receiving part is inhibited. A locking member is provided for properly decoupling the sleeves from the receiving part.

Description of the Related Art

Extension devices, also called head extenders, for pedicle screws for use in minimally invasive surgery are known in the art. For example, U.S. Pat. No. 7,563,264 B2 describes a spinal stabilization system for a minimally invasive procedure where detachable sleeves may be coupled to a collar of a bone anchor to allow for formation of the spinal stabilization system through a small skin incision. The detachable sleeves may allow for alignment of the collars to facilitate insertion of an elongated member in the collars. A coupling system is provided between the sleeve and the collar that inhibits translational movement of the sleeve relative to the collar. In one embodiment, the sleeve may be coupled to a collar of a bone fastener assembly with movable members that may be threaded into threaded openings in the collar.

WO 2013/112689 A2 describes a minimally invasive tower access device having an elongated outer sleeve that slidably receives an elongated inner sleeve. A lock nut is used to secure the inner sleeve and outer sleeve in a locked mode.

SUMMARY

Based on the above, there is still a need for an extension device for a bone anchor that is not only safe for use during surgical procedures, such as compression and/or distraction procedures, but that is also safe during the procedure of decoupling the extension device from the receiving part.

Embodiments of the invention provide an improved extension device or head extender for a bone anchor, in particular for use in minimally invasive surgery.

Embodiments of the invention also provide a system including such an extension device and a bone anchor that facilitates surgical procedures and improves safety.

In one embodiment, the extension device is configured to be coupled to a receiving part such that the extension device is locked against translational and rotational movement relative to the receiving part. Because translational and rotational movements of the extension device relative to the receiving part are inhibited, the connection between the extension device and the receiving part is more robust. The more secure connection permits safer placement or connection of a rod and a locking element for fixing or locking the rod to the receiving part. Surgical steps of adjustment of the spinal stabilization system, such as compression and/or distraction, can be performed using the extension device attached to the receiving part, for example, when the bone anchor is inserted into a bone. In one embodiment, the coupling between the extension device and the receiving part is achieved by a form-fit engagement of a portion of the extension device with a portion of the receiving part. In another embodiment, the coupling between the extension device and the receiving part is achieved by a frictional engagement, for example, a friction-fit engagement, of a portion of the extension device with a portion of the receiving part. The coupling can also be achieved, for example, by a combination of the form-fit coupling and the friction-fit coupling.

In one embodiment, the extension device includes a first sleeve, a second sleeve positioned within the first sleeve, and an interlocking bushing. The interlocking bushing connects the second sleeve to the first sleeve and provides controlled axial movement of the second sleeve relative to the first sleeve. After the extension device has been attached to a receiving part, the first sleeve and the second sleeve can be interlocked relative to each other and to the receiving part by moving the interlocking bushing in a first direction. The interlocking connection between the first sleeve and the second sleeve can be released by moving the interlocking bushing in a direction opposite to the first direction.

In one embodiment, translational movement between the extension device and the receiving part can be inhibited by a form-fit engagement between a circumferential rib that extends at least partially around a longitudinal axis of the extension device and a corresponding circumferential groove. The first sleeve may include the rib and the receiving part may include the groove, or vice versa.

In another embodiment, the first sleeve may be coupled to the receiving part by a form-fit connection and the second sleeve may be coupled to the receiving part by just a friction-fit connection, or vice versa.

In one embodiment, decoupling the extension device from the receiving part can be performed only in a prescribed sequence of steps. Decoupling may include a first step of decoupling the second sleeve from the receiving part and a second step of decoupling the first sleeve from the receiving part. The correct sequence of steps can be guaranteed by having a locking member that, in a first configuration, inhibits decoupling of the first sleeve from the receiving part when the second sleeve is still coupled to the receiving part. When the locking member is in a second configuration after decoupling the second sleeve from the receiving part, decoupling of the first sleeve from the receiving part may then be possible. As such, damage to the extension device based on incorrect use can be prevented. Moreover, by using such an extension device, the surgeon can perform subsequent steps in the surgical procedure only after correct decoupling of the extension device from the receiving part. This enhances the safety of the surgical procedure.

In one embodiment, the extension device may include a third sleeve that can be removably connected to the first sleeve to provide an extension device having an increased length. For example, a surgical procedure may begin by using a longer extension device with the third sleeve attached to the first sleeve for placement of the rod and the locking element. Thereafter, the third sleeve may be removed from the extension device to improve the placement of the receiving part relative to the rod, for example, during compression and distraction. With shorter extension devices without the third sleeves, there is more space so that multiple receiving parts may be oriented relative to each other with a greater range of angles therebetween.

The extension device includes relatively few parts or components, which facilitates easier assembly and operation of the extension device.

The extension device may be used together with a release or decoupling instrument adapted to engage the extension device. In one embodiment, the locking member of the extension device is configured to be engaged by the decoupling instrument only when the locking member is in the second configuration. In this embodiment, the locking member cannot be engaged by the extension device in the first configuration, where both the first and second sleeves are coupled to the receiving part. As such, a system of the extension device and the decoupling instrument provides safer handling and prevents damage to parts of the extension device or the receiving part.

In one embodiment, a spinal stabilization system includes at least two bone anchors with receiving parts that are adapted to be used with the extension device.

BRIEF DESCRIPTION OF THE DRAWINGS

Further features and advantages of the invention will become apparent from the description of embodiments using the accompanying drawings. In the drawings:

FIG. 1 shows an exploded perspective view of an extension device according to a first embodiment of the invention;

FIG. 2 shows a partially exploded perspective view of the extension device of FIG. 1 in an assembled state, with a detached optional third sleeve;

FIG. 3 shows a perspective view of the extension device of FIG. 2 in an assembled state;

FIG. 7b shows an enlarged view of a detail of FIG. 7a;

FIG. 8a shows a perspective view of a first sleeve of the extension device of FIGS. 1 to 4;

FIG. 8b shows a perspective view from below a front end portion of the first sleeve of FIG. 8a;

FIG. 9 shows a top view of the first sleeve of FIGS. 8a and 8b;

FIG. 10 shows a cross-sectional view of the first sleeve of FIGS. 8a to 9, the cross-section taken along line B-B in FIG. 9;

FIG. 11 shows a cross-sectional view of the first sleeve of FIGS. 8a to 10, the cross-section taken along line D-D in FIG. 10;

FIG. 12a shows a perspective view of a second sleeve of the extension device of FIGS. 1 to 4;

FIG. 12b shows an enlarged perspective view from below a front end portion of the second sleeve of FIG. 12a;

FIG. 13 shows a cross-sectional view of the second sleeve of FIGS. 12a and 12b, the cross-section taken along a plane including a longitudinal axis of the second sleeve and extending through centers of the legs of the second sleeve;

FIG. 14 shows an exploded perspective view of an interlocking bushing and an end portion of the second sleeve of the extension device of FIGS. 1 to 4;

FIG. 15 shows a perspective view of the interlocking bushing and the end portion of the second sleeve of FIG. 14 in an assembled state;

FIG. 16 shows a top view of the interlocking bushing of FIGS. 14 and 15;

FIG. 17 shows a cross-sectional view of the interlocking bushing of FIGS. 14 to 16, the cross-section taken along line E-E in FIG. 16;

FIG. 23a shows a cross-sectional view of a first step of coupling the extension device of FIGS. 1 to 4 to a receiving part of a bone anchor;

FIG. 23b shows a cross-sectional view of an upper portion of the extension device of FIGS. 1 to 4 in the first step according to FIG. 23a, where the interlocking bushing is in a second configuration;

FIG. 24a shows a cross-sectional view of a second step of coupling the extension device of FIGS. 1 to 4 to the receiving part of the bone anchor;

FIG. 24b shows a cross-sectional view of the upper portion of the extension device of FIGS. 1 to 4 in the second step according to FIG. 24a, where the interlocking bushing is still in the second configuration;

FIG. 25a shows a cross-sectional view of a third step of coupling the extension device of FIGS. 1 to 4 to the receiving part of the bone anchor;

FIG. 25b shows a cross-sectional view of the upper portion of the extension device of FIGS. 1 to 4 in the third step according to FIG. 25a, where the interlocking bushing is in a first configuration.

DETAILED DESCRIPTION

Figure 4:
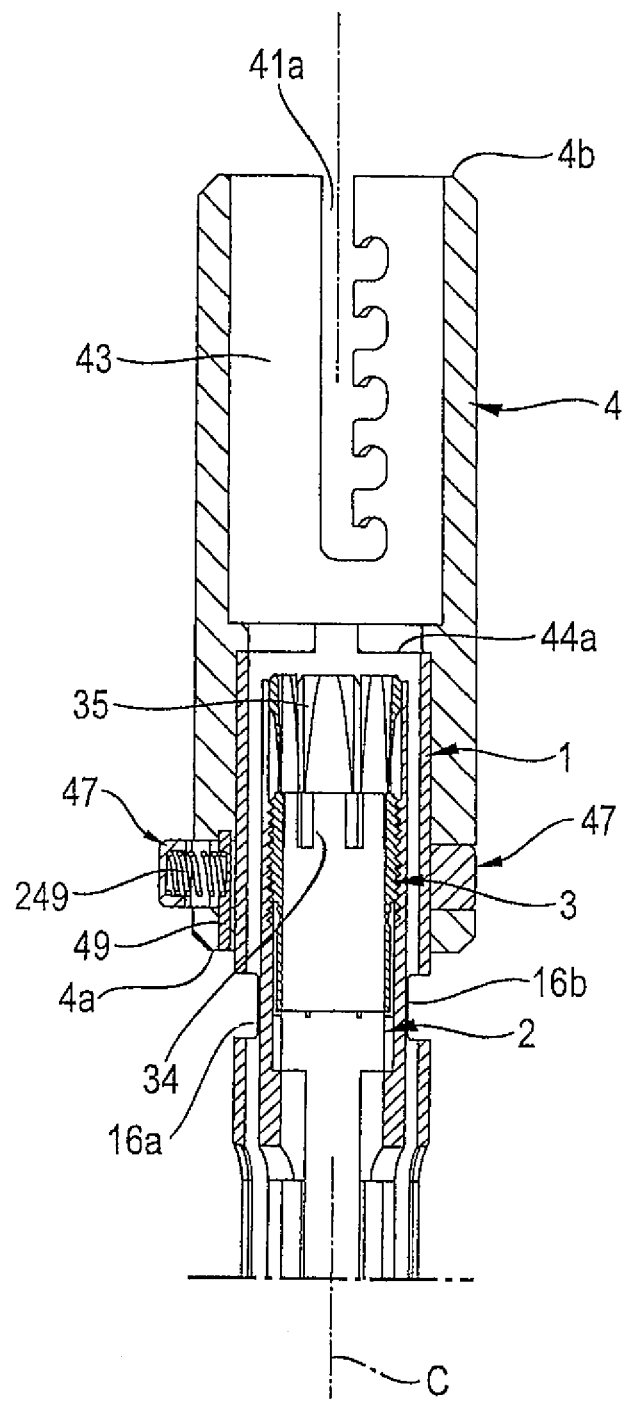
FIG. 4 shows a cross-sectional view of an upper portion of the extension device of FIGS. 2 and 3 with the attached third sleeve, the cross-section taken along a plane including a longitudinal axis of the extension device.
Figure 5:
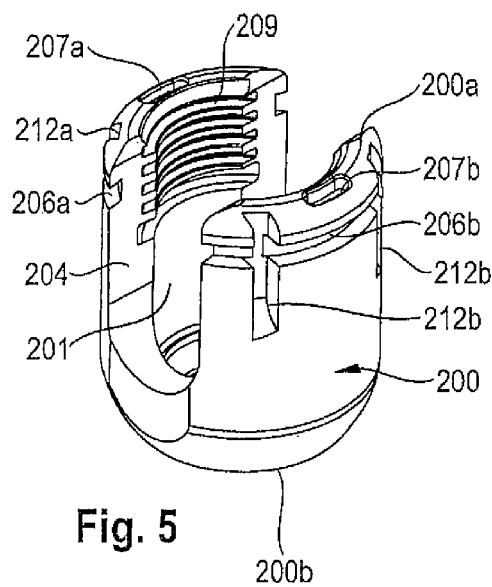
FIG. 5 shows a perspective view of an embodiment of a receiving part of a polyaxial bone anchor that, together with the extension device of FIGS. 1 to 4, forms a first embodiment of a system including an extension device and a bone anchor.
Figure 6:
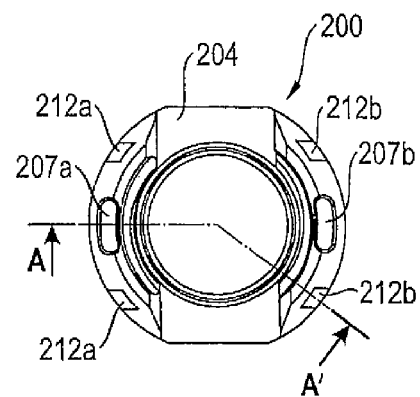
FIG. 6 shows a top view of the receiving part of FIG. 5.
Figure 7A:
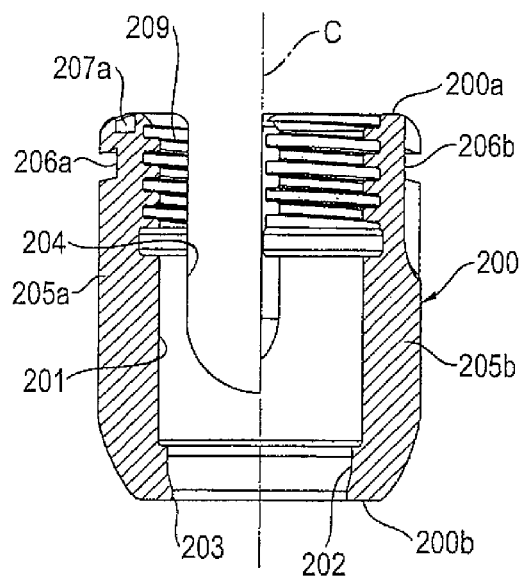
FIG. 7a shows a cross-sectional view of the receiving part of FIGS. 5 and 6, the cross-section taken along line A-A' in FIG. 6.
Figure 7B:
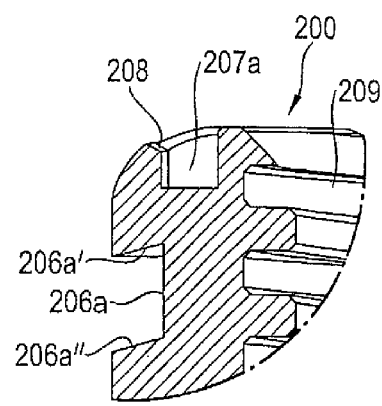

As shown in FIGS. 1 to 3, an extension device according to a first embodiment includes a first sleeve 1 that forms an outer sleeve, a second sleeve 2 that forms an inner sleeve and that is positionable within the first sleeve 1, and an interlocking bushing 3. The interlocking bushing 3 is configured to be connected to the second sleeve 2 and is configured to couple the second sleeve 2 to the first sleeve 1 to permit controlled motion of the second sleeve 2 relative to the first sleeve 1. In addition, the extension device may also include a third sleeve 4. The third sleeve 4 can be removably attached to the first sleeve 1 to extend a length of the entire extension device. When the first sleeve 1 and the second sleeve 2 are assembled as shown in FIGS. 2 and 3, the extension device can be used to place or implant parts of a spinal stabilization system in a patient's body, for example, using a minimally invasive procedure. For some particular steps in surgical procedures, the third sleeve 4 may be removed or omitted from the rest of the extension device.

The extension device shown in FIGS. 1 to 3 is configured to be used with a bone anchor, for example, a polyaxial bone anchor with a pedicle screw. As depicted in FIGS. 5 to 7b and 23a to 25b, an embodiment of such a bone anchor may include an anchoring element with a threaded shank 100 and a spherical segment-shaped head 101. The anchoring element is configured to be pivotably coupled to a receiving part 200. The receiving part 200 is shown in more detail in FIGS. 5 to 7b. The receiving part 200 may be formed as a substantially cylindrical part with a first end or top end 200a, a second end or bottom end 200b, a central axis C, a coaxial bore 201 extending from the top end 200a to a distance from the bottom end 200b, and a seat 202 for receiving the head 101 of the anchoring element. The receiving part 200 may further include a lower opening 203 at the bottom end 200b where the threaded shank 100 of the bone anchoring element can pass through. A substantially U-shaped recess 204 for receiving a rod therein may extend from the top end 200a towards the bottom end 200b. The recess 204 forms two free legs 205a, 205b. In addition, circumferentially extending grooves 206a, 206b are formed at an outer surface of the legs 205a, 205b at a distance from the top end 200a. The circumferentially extending grooves 206a, 206b each extend around an outer surface of the corresponding leg 205a, 205b from one end of a channel formed by the U-shaped recess 204 to a second end of the channel and have ends that are open towards the U-shaped recess 204. Upper sidewalls 206a', 206b' and lower sidewalls 206a", 206b" of the grooves 206a, 206b may have shapes that are inclined radially outwardly in a direction towards the bottom end 200b of the receiving part 200, as shown, for example, in FIG. 7b.

The receiving part 200 may further include recesses 207a, 207b at the top end 200a at a free end surface of each of the legs 205a, 205b. The recesses 207a, 207b respectively extend into the legs 205a, 205b in a direction parallel to the central axis C of the receiving part 200. When viewed from a top view of the receiving part 200, the recesses 207a, 207b are elongate and closed at both ends in a circumferential direction. Both recesses 207a, 207b serve to engage a portion of the extension device, as further described below. A chamfered section 208 may be provided at a top end of each of the recesses 207a, 207b to facilitate engagement of the recesses 207a, 207b with corresponding projections of the extension device.

In addition, the receiving part 200 may have a pair of longitudinal grooves 212a at one side of the U-shaped recess 204 and a pair of longitudinal grooves 212b at an opposite side of the U-shaped recess 204. Each respective pair of grooves 212a, 212b are spaced apart from each other in the circumferential direction. The grooves 212a, 212b are located on either side of the respective recesses 207a, 207b. Moreover, the grooves 212a, 212b extend from the top end 200a at outer walls of the receiving part 200 toward the bottom end 200b. The grooves 212a, 212b are open towards the top end 200a and have a decreasing depth towards opposite closed ends located at a distance from the top end 200a. The cross-sections of the longitudinal grooves 212a, 212b are substantially rectangular. As illustrated in particular in FIG. 5, the longitudinal grooves 212a, 212b intersect the circumferentially extending grooves 206a, 206b. The grooves 212a, 212b may interact with corresponding longitudinally extending pairs of ribs of the first sleeve 1 of the extension device, described in greater detail below, to provide a form-fit connection between the receiving part 200 and the first sleeve 1.

An internal thread 209 may be provided at an upper portion of the legs 205a, 205b for cooperating with a locking screw or element (not shown) for fixing the rod relative to the receiving part 200.

Referring to FIGS. 8a to 11, the first sleeve 1 of the extension device is elongate and has a longitudinal axis c that is coaxial with the central axis C of the receiving part 200 when the extension device is coupled to the receiving part. The first sleeve 1 further has a front end 1a and a rear end 1b.

Adjacent to the rear end 1b, the first sleeve 1 has a first section 11 with an inner diameter that is greater than an inner diameter of a following second section 12. Two small projections 11a, 11b protrude from the rear end 1b of the first sleeve 1 that may interact with recesses in the third sleeve 4 for correct positioning of the third sleeve 4 onto the first sleeve 1. The second section 12 provides a clamping portion for the interlocking bushing 3 as further described below. Adjacent to the second section 12, a third section 13 is provided that may have a slightly smaller inner diameter as compared to the second section 12. An internal thread or internally threaded section 14 is provided in the third section 13 that is configured to interact with the interlocking bushing 3. The internally threaded section 14 is preferably adjacent to the second section 12. As shown in FIGS. 9 and 11, portions of the first sleeve 1 that are offset from the projections 11a, 11b, for example, 90° offset, may be double-walled due to the presence of arc-shaped or cylinder segment-shaped longitudinal recesses 19c, 19d.

An outer wall of the first sleeve 1 may further include two opposite first transverse recesses 15a, 15b at a first distance from the rear end 1b. The first recesses 15a, 15b serve for attaching an instrument to the first sleeve 1. The first recesses 15a, 15b may be located at circumferential positions around the first sleeve 1 that correspond to the small projections 11a, 11b. Moreover, at a second distance from the rear end 1b, two second transverse recesses 16a, 16b may be provided that extend in a circumferential direction and that are substantially 90° offset from the first recesses 15a, 15b. The second transverse recesses 16a, 16b extend fully through an outermost wall of the first sleeve 1 and may provide access to the recesses 19c, 19d, for example, for cleaning purposes.

The first sleeve 1 includes two elongate substantially U-shaped slits 17a, 17b, as shown, for example, in FIG. 8a. The U-shaped slits 17a, 17b have a reverse or inverted U-shape as compared to the recess 204 in the receiving part 200 when the receiving part 200 is attached to the extension device. The U-shaped slits 17a, 17b are offset from each other by 180° and extend from the front end 1a of the first sleeve 1 towards the rear end 1b with an upper end that is a distance from the second section 12 of the first sleeve 1. The longitudinal slits 17a, 17b have a width in a circumferential direction that is greater than a diameter of a spinal stabilization rod such that the slits 17a, 17b permit the rod to be passed through the slits. The width of the slits 17a, 17b may be substantially the same as the width of the U-shaped recess 204 of the receiving part 200. The length of the slits 17a, 17b may be more than ⅓ of the length of the first sleeve 1, and preferably more than ½ of the length of the first sleeve 1. In one embodiment, the length of the slits 17a, 17b may be longer than ¾ of the length of the first sleeve 1. The slits 17a, 17b are located at circumferential positions that are respectively offset by approximately 90° from the circumferential positions of the first recesses 15a, 15b. The slits 17a, 17b form two free legs 18a, 18b that interact with the free legs 205a, 205b of the receiving part 200. The legs 18a, 18b of the first sleeve 1 are slightly flexible in a direction perpendicular to the sleeve axis, such that the first sleeve 1 can be snapped onto the legs 205a, 205b of the receiving part 200.

At each of the legs 18a, 18b, an inner surface of the third section 13 of the first sleeve 1 has longitudinally extending substantially arc-shaped or cylinder segment-shaped guiding recesses 19a, 19b. Portions of the second sleeve 2 are configured to be guided in the guiding recesses 19a, 19b, as discussed in greater detail below. The guiding recesses 19a, 19b extend in the longitudinal direction towards the rear end 1b beyond the slits 17a, 17b, as can be seen in particular in FIG. 10.

Figure 18:
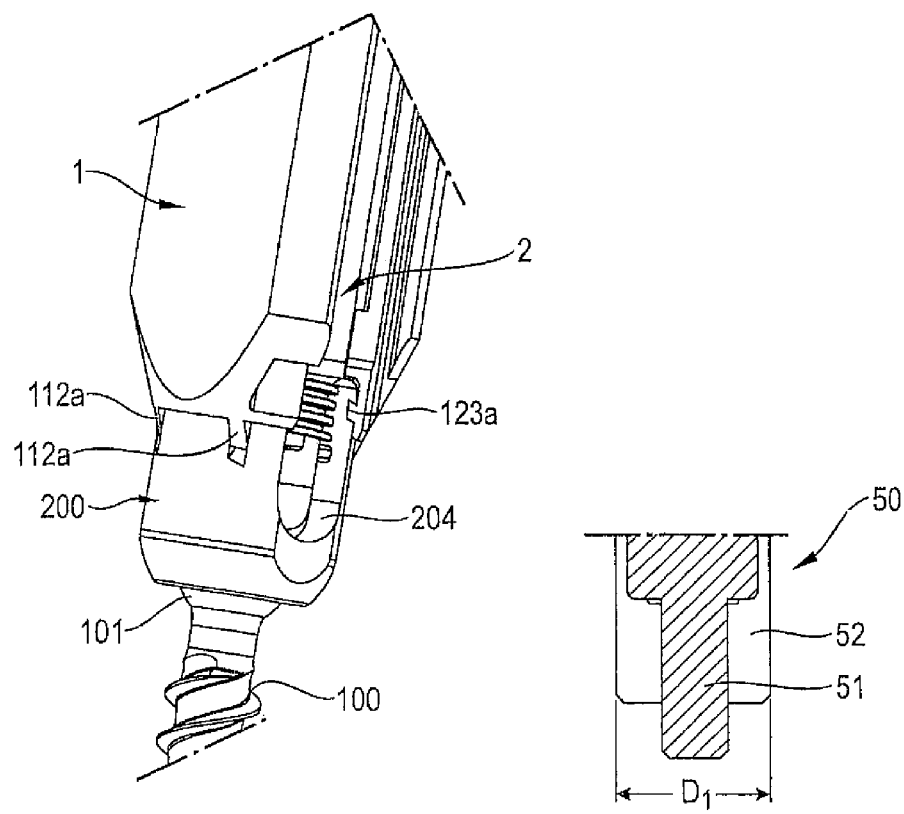
FIG. 18 shows a perspective view of a polyaxial bone anchor with a receiving part and a front portion of the extension device according to the first embodiment coupled to the receiving part.

At a distance from the front end 1a, each of the legs 18a, 18b has an inwardly directed projection 120a, 120b that extends in a circumferential direction around the longitudinal axis c from one slit 17a to the opposite slit 17b, as best seen in FIG. 8b. The shape of the circumferential projections 120a, 120b is substantially complementary to the shape of the circumferential grooves 206a, 206b of the receiving part 200, as can be seen in particular in FIGS. 18, 24a, and 25a.

Upper surfaces of the projections 120a, 120b that face towards the rear end 1b may be inclined towards the rear end 1b with a slope that matches the complementary inclined upper sidewalls 206a', 206b' of the grooves 206a, 206b. Lower surfaces of the circumferential projections 120a, 120b may be perpendicular to the longitudinal axis c or similarly inclined towards the rear end 1b. The inclination of one or more of the surfaces of the projections 120a, 120b facilitates engagement of the projections 120a, 120b into the respective grooves 206a, 206b when the first sleeve 1 is coupled to the receiving part 200.

In addition, the first sleeve 1 includes a pair of ribs 112a on the leg 18a and a pair of ribs 112b on the leg 18b. The pairs of ribs 112a, 112b are circumferentially located at positions that correspond to the circumferential positions of the longitudinal grooves 212a, 212b of the receiving part 200. The ribs 112a, 112b respectively protrude inward from the legs 18a, 18b and downward from the front end 1a, and have a shape that substantially matches the shape of the grooves 212a, 212b of the receiving part 200. As can be seen in particular in FIG. 8b, an outer surface of each of the ribs 112a, 112b tapers radially inwardly towards the free ends of the ribs, such that the cross-section of the ribs 112a, 112b is substantially triangular when viewed in the circumferential direction.

Transverse thickened rib portions 123a, 123b extend outwardly in a circumferential direction from each of the longitudinal ribs 112a, 112b. The transverse rib portions 123a, 123b are located at a distance from the front end 1a of the first sleeve 1 that corresponds to an axial position of the circumferentially extending grooves 206a, 206b on the receiving part 200. Hence, the transverse rib portions 123a, 123b are located at the same distance from the front end 1a of the first sleeve 1 as the circumferential projections 120a, 120b.

Due the longitudinal ribs 112a, 112b that are configured to respectively engage the longitudinal grooves 212a, 212b, the strength of the connection between the extension device and the receiving part 200 is enhanced. The longitudinal ribs 112a, 112b and grooves 212a, 212b allow a high torque to be applied to the receiving part by the extension device.

A general outer shape of the first sleeve 1 may be cylindrical. Flattened outer surface portions 122a, 122b may be provided at respective outer surfaces of the legs 18a, 18b, for example, for interacting with a tool (not shown).

The total length of the first sleeve 1 is such that when the bone anchor is inserted into a bone and the first sleeve 1 is attached to the receiving part 200, the extension device protrudes a sufficient extent from the operation site.

As illustrated in FIGS. 12a to 13, the second sleeve 2 includes a front end 2a and an opposite rear end 2b. The second sleeve 2 may have a substantially constant outer diameter. Adjacent to the rear end 2b, the second sleeve 2 has a first portion 21 with a circumferentially closed cylinderical surface. The first portion 21 is configured to engage the interlocking bushing 3. A plurality of longitudinal slits 22 that are open to the rear end 2b and extend to a distance from the rear end 2b are provided in the first portion 21. The plurality of slits 22 render the first portion 21 flexible such that the first portion 21 can elastically snap onto a portion of the interlocking bushing 3 and hold the interlocking bushing 3 therein by friction. An inwardly extending annular projection 23 is provided at a first distance from the rear end 2b. The annular projection 23 interacts with a corresponding depression or groove at the interlocking bushing 3 to inhibit inadvertent removal of the interlocking bushing 3 from the second sleeve 2. At a second distance from the rear end 2b that is greater than the first distance, a stop 21a is provided, for example in the form of an annular shoulder. The stop 21a limits how far the interlocking bushing 3 can be inserted into the second sleeve 2 and forms an abutment for the interlocking bushing 3 when the interlocking bushing 3 is screwed downward into the first sleeve 1. An outer diameter of the first portion 21 of the second sleeve 2 is smaller than an inner diameter of the third section 13 of the first sleeve 1.

The second sleeve 2 includes two recesses 24a, 24b with substantially rectangular cross-sections that extend from the front end 2a through the second sleeve 2 up to the first portion 21. The recesses 24a, 24b have a size such that two opposite legs 25a, 25b are formed that fit into the guiding recesses 19a, 19b of the first sleeve 1. The legs 25a, 25b have a length such that they extend beyond the upper closed ends of the slits 17a, 17b of the first sleeve 1 in a direction towards the rear end 1b of the first sleeve 1 when the second sleeve 2 is inserted into the first sleeve 1.

The front end 2a of the second sleeve 2 has substantially flat surface portions 26a, 26b on each of the legs 25a, 25b. The flat surface portions 26a, 26b are configured to cooperate with substantially flat surface portions on the top end 200a of the receiving part. Moreover, the front end 2a includes projections 27a, 27b on each of the legs 25a, 25b, respectively, that are configured to cooperate with the recesses 207a, 207b at the free ends of the legs 205a, 205b of the receiving part 200. The projections 27a, 27b have a substantially complementary shape to the shape of the respective recesses 207a, 207b. Inner surfaces of the projections 27a, 27b that face toward a longitudinal axis of the second sleeve 2 are flush with the inner surfaces of other portions of the legs 25a, 25b. In addition, outer surfaces of the projections 27a, 27b are slightly recessed with respect to outer surface of other portions of the legs 25a, 25b. The overall shape of the projections 27a, 27b is substantially arc-shaped with rounded edges corresponding to the recesses 207a, 207b in the receiving part 200. Moreover, in a circumferential direction, the projections 27a, 27b are each arranged substantially in the middle of each respective leg 25a, 25b.

Turning now to FIGS. 14 to 17, the interlocking bushing 3 has a front end 3a, a rear end 3b, and a cylindrical section 31 adjacent to the front end 3a. The cylindrical section 31 may have a smooth outer surface. An outer diameter of the cylindrical section 31 may be substantially equal to an inner diameter of the first portion 21 of the second sleeve 2 such that the interlocking bushing 3 is held in the second sleeve 2 by friction. Adjacent to the cylindrical section 31, the interlocking bushing 3 has a groove 32 that interacts with the annular projection 23 of the second sleeve 2. Following the groove 32, the interlocking bushing 3 has a threaded portion 33 with an external thread that is configured to interact with the threaded section 14 of the first sleeve 1.

The interlocking bushing 3 has a through bore. The portion of the bore corresponding to the threaded portion 33 of the interlocking bushing 3 has an inner diameter that is slightly larger than $D_1$, where $D_1$ corresponds to an outer diameter of a decoupling instrument. The interlocking bushing 3 has a plurality of longitudinal engagement grooves 34 for engagement with a driver. The longitudinal engagement grooves 34 are located at an inner wall of the interlocking bushing 3 at an upper region of the threaded portion 33. Adjacent to the rear end 3b, the interlocking bushing 3 has a collet portion 35 with a plurality of substantially longitudinal slits 36 that are open towards the rear end 3b. The slits 36 render the collet portion 35 flexible such that the collet portion 35 can be radially compressed by exerting pressure thereto from the outside. The collet portion 35 includes a thickened annular portion 37 at the rear end 3b of the interlocking bushing 3. As shown in FIG. 15, the thickened annular portion 37 has a lower side 37a that tapers and narrows toward the front end 3a and an upper side 37b that tapers and narrows toward the rear end 3b such that a cross-section of the thickened portion 37 is substantially triangular. The length of the collet portion 35 is such that when the interlocking bushing 3 is screwed into the first sleeve 1 and the second sleeve 2 engages the receiving part 200, most of the length of the thickened portion 37 of the collet portion 35 is located within the second section 12 of the first sleeve 1, as depicted more in detail in FIG. 19. In this position, the collet portion 35 is slightly compressed by the inner wall of the first sleeve 1, such that an inner diameter $D_2$ of the collet portion 35 is smaller than $D_1$, as shown in detail in FIG. 19. When the interlocking bushing 3 is screwed backward in a direction away from the front end 1a, the collet portion 35 emerges from the second section 12 and into the larger diameter first section 11 of the first sleeve 1, whereby the collet portion 35 expands.

Hence, the collet portion 35 forms a locking member that can assume a first configuration and a second configuration. In the first configuration, when the second sleeve 2 engages the receiving part 200, the collet portion 35 is compressed and inhibits insertion of a tool therein for removing the first sleeve 1 from the receiving part 200. In the second configuration, when the second sleeve 2 is decoupled from the receiving part 200, the collet portion 35 is expanded and allows insertion of the tool therein for removing the first sleeve 1 from the receiving part 200. In this embodiment, the locking member is monolithically formed with the interlocking bushing 3.

The assembly of the second sleeve 2 and the interlocking bushing 3 is shown in FIGS. 14 and 15. The cylindrical section 31 of the interlocking bushing 3 can be pushed into the first portion 21 of the second sleeve 2 until the annular projection 23 of the second sleeve 2 snaps into the groove 32 of the interlocking bushing 3. As a result, the interlocking bushing 3 is coupled to the second sleeve 2 such that rotational motion of the interlocking bushing 3 relative to the second sleeve 2 is still possible. In addition, axial movement of the interlocking bushing 3 relative to the second sleeve 2 is inhibited due, for example, to the interlocking bushing 3 abutting against the stop 21a provided in the second sleeve 2.

The assembly, including the second sleeve 2 and the interlocking bushing 3 in a mounted state as shown in FIG. 15, is then inserted into the first sleeve 1 from the rear end 1b until the threaded portion 33 of the interlocking bushing 3 engages the threaded section 14 of the first sleeve 1. The legs 25a, 25b of the second sleeve 2 are guided in the guiding recesses 19a, 19b in the first sleeve 1. When the interlocking bushing 3 is secured into the threaded section 14 of the first sleeve 1, the connection between the second sleeve 2 and the first sleeve 1 via the interlocking bushing 3 is a rigid connection.

Figure 19:
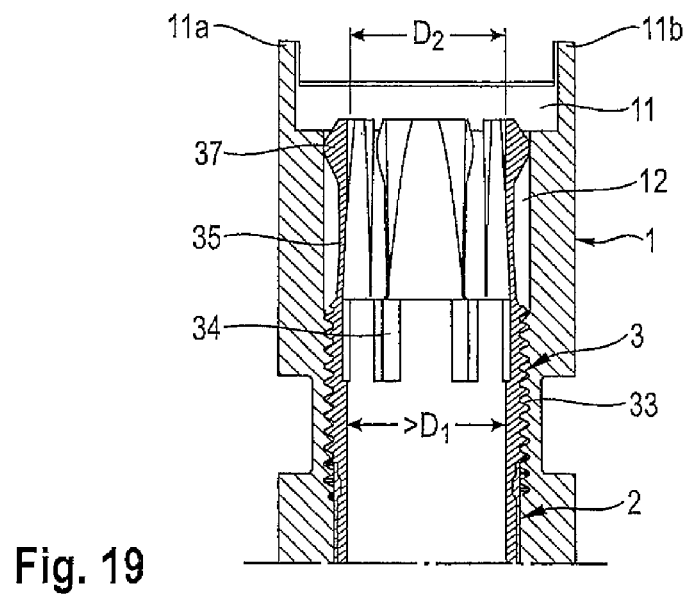
FIG. 19 shows a cross-sectional view of an upper portion of the extension device of FIGS. 1 to 4 without the third sleeve and a front end portion of a decoupling instrument adapted to be used with the extension device, the cross-section taken along a plane including the longitudinal axis of the extension device.

As depicted in FIG. 19, a release or decoupling instrument 50 (only a front portion of which is shown) includes an inner portion 51 and an outer portion 52 that slidably receives the inner portion 51. The outer portion 52 may be expandable and serves for decoupling the first sleeve 1 from the receiving part 200. The outer portion 52 has an outer diameter $D_1$ such that the outer portion 52 can be guided through the interlocking bushing 3 and into the first sleeve 1 when the collet portion 35 of the interlocking bushing 3 is not radially compressed. The outer portion 52 can be radially expanded inside the first sleeve 1. Thereby, the first sleeve 1 can be decoupled from the receiving part 200.

The decoupling instrument 50 can be inserted into the interlocking bushing 3 only when the collet portion 35 is in the second configuration in which the collet portion 35 protrudes outward of the second section 12 and into the first section 11 of the first sleeve 1. Because the first section 11 has a greater inner diameter than the second section 12, the collet portion 35 can radially expand in the first section 11 such that the expanded inner diameter of the collet portion 35 is sufficiently large to allow insertion of the decoupling instrument 50 into and through the collet portion 35.

Figure 20:
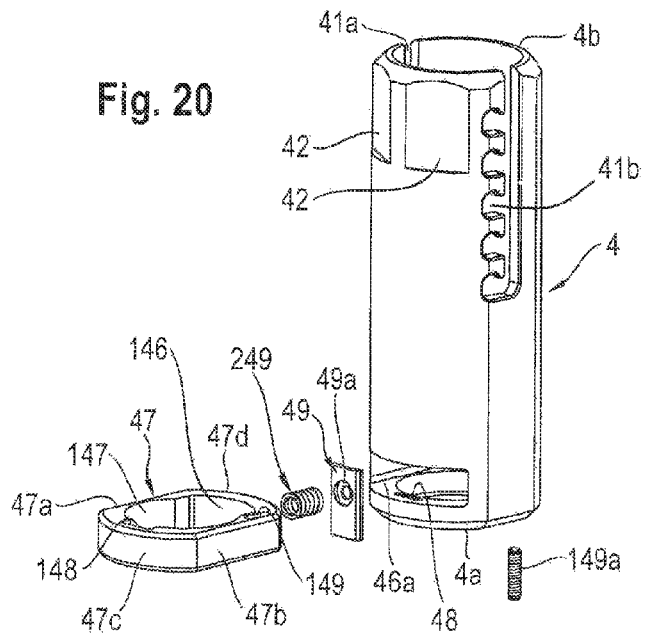
FIG. 20 shows an exploded perspective view of the third sleeve of the extension device of FIGS. 2 to 4.
Figure 21:
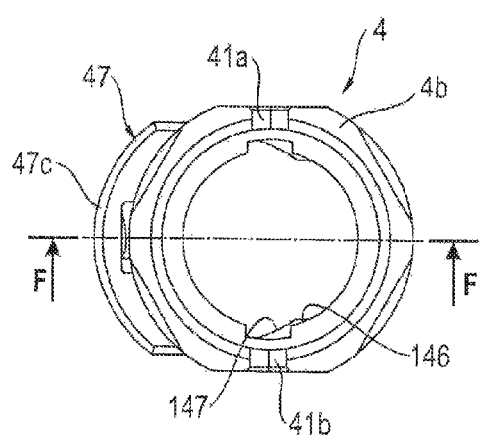
FIG. 21 shows a top view of the third sleeve of FIG. 20.
Figure 22:
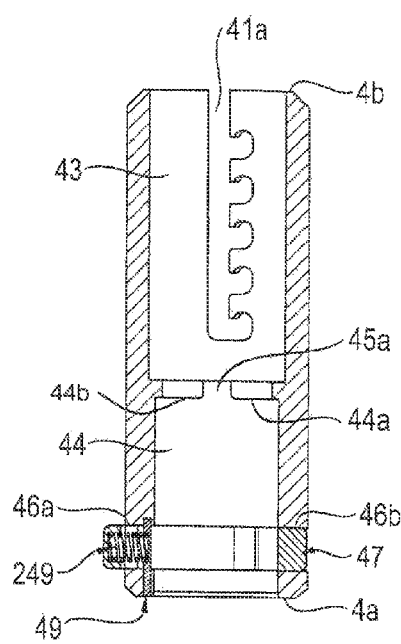
FIG. 22 shows a cross-sectional view of the third sleeve of FIGS. 20 and 21, the cross-section taken along line F-F in FIG. 21.

Referring to FIGS. 20 to 22, the optional third sleeve 4 will be further described. The third sleeve 4 has a first or front end 4a, a second or rear end 4b, and an outer diameter that may be greater than the outer diameter of the first sleeve 1. Adjacent to the rear end 4b, the third sleeve 4 has two opposite longitudinal slits 41a, 41b that extend from the second end 4b toward the first end 4a along at least a portion of the third sleeve 4. The longitudinal slits 41a, 41b, may be, for example, up to ½ of the length of the third sleeve 4. One of the sidewalls of each of the longitudinal slits 41a, 41b has a wavy structure for latching with a reduction sleeve (not shown) used for further steps in the surgical procedure, for example, for pressing down the rod and inserting a locking screw to fix the rod. Furthermore, an engagement structure 42, for example, a plurality of flat engagement portions, is provided at an outer surface of an upper portion of the third sleeve for applying a tool thereto.

The third sleeve 4 has a first inner portion 43 adjacent to the second end 4b and a second inner portion 44 adjacent to the first end 4a. The second inner portion 44 is configured to accommodate an upper portion at the rear end 1b of the first sleeve 1 therein. For this purpose, the inner diameter of the second portion 44 of the third sleeve 4 is slightly larger than the outer diameter of the upper portion of the first sleeve 1. An upper end of the second portion 44 may provide a shoulder 44a, 44b that forms an abutment for the rear end 1b of the first sleeve 1. The shoulder 44a, 44b may have interruptions 45a, 45b, such as slots or grooves, that correspond to the small projections 11a, 11b of the first sleeve 1. An inner diameter of the first portion 43 may be larger than an inner diameter of the second portion 44.

At a distance from the first end 4a, the third sleeve 4 has two transverse slots 46a, 46b at positions that are 180° offset from each other. The slots 46a, 46b are configured to accommodate an operating pusher 47 therein. The slots 46a, 46b are elongate in a circumferential direction and preferably offset 90° with respect to the longitudinal slits 41a, 41b. Moreover, a substantially rectangular recess 48 is at and extends from the bottom of one of the elongate transverse slots 46a for accommodating an abutment plate 49 therein.

The pusher 47 is a flat piece that can extend through the slots 46a, 46b of the third sleeve 4. The pusher 47 has two substantially parallel longitudinal outer walls 47a, 47b and two outwardly curved sidewalls 47c, 47d that connect the parallel longitudinal outer walls 47a, 47b, respectively. A total length from an outer end of one curved sidewall 47c to an outer end of the opposite curved sidewall 47d is greater than the outer diameter of the third sleeve 4 at the position of the transverse slots 46a, 46b. As such, a portion of the pusher 47 still protrudes out of at least one of the transverse slots 46a, 46b when the pusher is inserted into the slots 46a, 46b of the third sleeve 4. The inside of the pusher 47 is hollow to accommodate the upper portion of the first sleeve 1 therein. In more detail, the pusher 47 has a first inner portion 146 with an inner contour that matches an outer contour of the upper portion of the first sleeve 1. Adjacent to the first inner portion 146, the pusher 47 has a second inner portion 147 with an inner contour that is greater than an outer contour of the first sleeve 1.

The pusher 47 further includes a recess 148 at an inner side of the curved outer sidewall 47c for accommodating a spring 249. Furthermore, on one of the substantially flat longitudinal outer walls 47a, 47b, an elongate hole 149 is provided that may be near the curved sidewall 47d. The elongate hole 149 is elongate in a lengthwise direction of the pusher 47, which is the direction in which the pusher 47 can be moved relative to the third sleeve 4. A securing element 149a, such as a headless screw, extends through the wall of the third sleeve 4 into the elongate hole 149. The securing element 149a limits or constrains the path of movement of the pusher 47 relative to the third sleeve 4 and prevents the pusher 47 from being removed from the third sleeve 4.

The spring 249 may be a helical spring as shown, or any other suitable kind of spring. The spring 249 is positioned in the recess 148 of the pusher 47 and extends into a countersink 49a in the abutment plate 49.

The spring 249 is biased such that it holds the pusher 47 in a position in which one curved sidewall 47c protrudes outward from the transverse slot 46a and the opposite curved sidewall 47d is within the opposite slot 46b. In this position, the second inner portion 147 of the pusher 47, that has the larger inner diameter compared to the first inner portion 146, is partially narrowed by the third sleeve 4, as can be seen in FIG. 21. As such, in this position, the first sleeve 1 fits into the second inner portion 44 of the third sleeve 4 and is held therein via the pusher 47 due to friction, as can be seen in FIG. 4. To remove the third sleeve 4 from the first sleeve 1, a portion of the pusher 47 that protrudes outward from the slot 46a is pushed against the force of the spring 249 into the slot 46a, thereby compressing the spring 249 and forcing the opposite curved sidewall 47d to protrude from the opposite slot 46b. Due to the movement of the pusher 47, the second inner portion 147 of the pusher 47, that has a larger diameter than the upper portion of the first sleeve 1, is brought into a position around and aligned with the first sleeve 1. In this position, the third sleeve 4 can be removed from around the first sleeve 1 by pulling the third sleeve 4 from the first sleeve 1.

The mounting of the third sleeve 4 onto the first sleeve 1 may be performed in a similar manner as the removal process, by pushing the pusher 47 into the slot 46a and placing the third sleeve 4 onto the first sleeve 1.

The parts of the extension device are all made of a body-compatible material, such as titanium or stainless steel, a body-compatible metal alloy, for example a Ti—Ni alloy, such as Nitinol, or a body-compatible plastic material, such as polyether ether ketone (PEEK). The parts may all be made of the same material or of different materials.

Referring now to FIGS. 18 to 25b, the attachment of the extension device to a bone anchor will be further described. As shown in FIG. 23a, the front end 1a of the first sleeve 1 of the extension device is moved toward the receiving part 200. Then, the legs 18a, 18b of the first sleeve 1 are spread to a certain extent when they touch and are pushed against the top end 200a of the receiving part 200. Due to further downward movement of the extension device, the circumferential projections 120a, 120b of the legs 18a, 18b snap into the circumferential grooves 206a, 206b of the receiving part 200. Also, the vertical ribs 112a, 112b of the first sleeve 1 engage the corresponding vertical grooves 212a, 212b of the receiving part 200. During coupling of the first sleeve 1 to the receiving part 200, the coupled second sleeve 2 and interlocking bushing 3 are in a retracted position in which the collet portion 35 of the interlocking bushing 3 extends into the first section 11 of the first sleeve 1. This configuration is shown in FIGS. 23a to 24b. The thickened upper portion 37 of the collet portion 35 protrudes out of the second section 12 of the first sleeve 1 and into the first section 11 of the first sleeve 1. In this configuration, an inner diameter of the collet portion 35 is at least a diameter greater than $D_1$, which corresponds to an inner diameter of the threaded portion 33 of the interlocking bushing 3.

Then, as shown in FIGS. 25a and 25b, the second sleeve 2 is moved relative to the first sleeve 1 towards the receiving part 200 by screwing the interlocking bushing 3 further towards the front end 1a of the first sleeve 1. When the projections 27a, 27b of the second sleeve 2 enter the corresponding recesses 207a, 207b at the top end 200a of the receiving part 200, rotational movement of the second sleeve 2 relative to the first sleeve 1 and to the receiving part 200 is further inhibited. At the same time, the tapered upper thickened portion 37 of the collet portion 35 slides along the shoulder formed by the transition between the first section 11 and the second section 12 of the first sleeve 1 until the thickened portion 37 enters the second section 12 of the first sleeve 1. Thereby, the collet portion 35 of the interlocking bushing 3 is radially compressed as shown in FIG. 25b. An upper inner diameter of the collet portion 35 is now a diameter $D_2$ which is less than the diameter $D_1$. The second sleeve 2 can rotate relative to the interlocking bushing 3 such that the rotational alignment between the legs 18a, 18b of the first sleeve 1 and the legs 25a, 25b of the second sleeve 2 is maintained. Further rotation of the interlocking bushing 3 toward the front end 1a of the first sleeve 1 presses the flat surface portions 26a, 26b of the front end 2a of the second sleeve 2 onto the free flat end surfaces of the receiving part 200. By this engagement of the second sleeve 2 with the receiving part, and by the engagement of the projections 120a, 120b and ribs 112a, 112b of the first sleeve 1 with the grooves 206a, 206b, 212a, 212b of the second sleeve 2, respectively, the receiving part 200, and the second sleeve 2 are interlocked to provide a safe and strong connection between the extension device and the receiving part 200. In such a configuration, insertion of the rod and the locking screw can take place, as well as surgical steps thereafter, such as compression and distraction steps using the extension device.

Meanwhile, in the configuration shown in FIG. 25b, the decoupling instrument with an outer diameter $D_1$ cannot be inserted into the interlocking bushing 3. Therefore, the collet portion 35 of the interlocking bushing 3 acts as a locking member that prevents decoupling of the extension device from the receiving part 200 when the second sleeve 2 is also coupled to the receiving part 200. This enhances the safety of the procedure and prevents damage to portions of the extension device, in particular, to the second sleeve 2.

Rotating the interlocking bushing 3 in an opposite direction moves the interlocking bushing 3 away from the front end 1a of the first sleeve 1, releases the interlocking connection, and permits retraction of the projections 27a, 27b of the second sleeve out of the recesses 207a, 207b.

Figure 26:
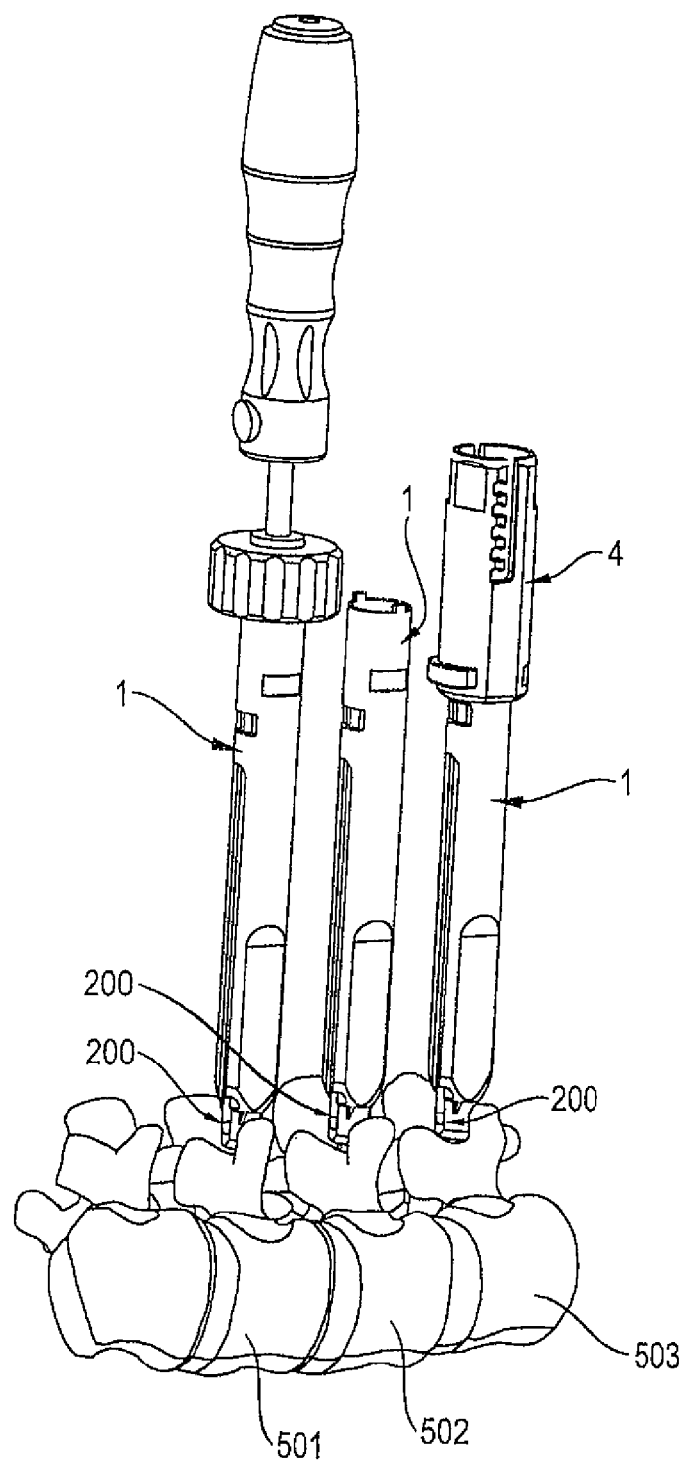
FIG. 26 shows a perspective view of a system including a plurality of bone anchors with receiving parts and extension devices having different lengths coupled thereto.

In clinical use, as shown in FIG. 26, the extension device is attached to the receiving part 200 of a bone anchor. The bone anchor is inserted through a minimally invasive procedure into a pedicle of a vertebra. As an example, three vertebrae 501, 502, 503 are shown with bone anchors and extension devices mounted thereto. By rotating the extension devices with the aid of an instrument, the U-shaped recesses 204 of the receiving parts 200 of the bone anchors can be aligned to permit insertion of a rod. Because the connections between the receiving parts 200 and the extension devices are robust and safe, an easy alignment using the extension devices is possible. Thereafter, the rod is inserted through the slits 17a, 17b of the extension devices (not shown) and fixed with a locking screw that is guided through the extension device until the locking screw can be screwed between the legs 205a, 205b of the receiving part 200. By applying an instrument to the extension device, compression and/or distraction procedures can also be performed using a minimally invasive technique. Using only the first sleeve 1 and the second sleeve 2 without the third sleeve 4 has the advantage that the extension devices have a greater distance between each other and that a greater angle between one extension device and another extension device can be achieved. The third sleeve 4 may be used in situations in which the surgeon has to approximate the rod.

Other modifications of the above described embodiments may also be contemplated. It shall be noted that the shapes of the engaging complementary structures of the first sleeve and the receiving part, as well as of the second sleeve and the receiving part, can be modified and are not limited to the exact shapes shown in the embodiments. In a further modification, the second sleeve may be coupled to the receiving part by only frictional engagement between a portion of the second sleeve and a portion of the receiving part. For example, a front end surface of the second sleeve may be pressed against a free end surface of the legs 205a, 205b of the receiving part. In a further modification, the first sleeve may be coupled to the receiving part by such a friction-fit.

The function of the first and the second sleeve may be interchanged. In such an embodiment, the locking member inhibits the decoupling of the second sleeve when the first sleeve is still coupled to the receiving part.

The extension device can also be used with any bone anchor that includes a receiving part, such as polyaxial bone anchors and/or monoaxial bone anchors, and can also be used with receiving parts having different shapes. Anchors with inner compression members or outer rings may be used with the extension device, so long as an engagement structure at the receiving part is provided that can cooperate with a corresponding engagement structure of the extension device.

The locking member in the form of a collet portion is shown as a monolithic part of the interlocking bushing. However, a locking member can also be a separate member, for example a separate collet. Other suitable kinds of locking members that can be actuated by actuating the second sleeve can also be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. An extension device for a bone anchor, wherein the bone anchor comprises an anchoring section for anchoring to a bone and a receiving part configured to be connected to the anchoring section, the receiving part comprising two legs defining a channel for receiving a rod, the extension device comprising:
   a first sleeve having a first end, a second end, and a first sleeve axis extending between the first and second ends, wherein the first end of the first sleeve is configured to be coupled to the receiving part;
   a second sleeve positionable at least partially in and movable axially relative to the first sleeve, wherein the second sleeve is configured to be coupled to the receiving part; and
   a locking member movable relative to the second sleeve, the locking member having a through bore, wherein the locking member is configured to be connected to the first sleeve at a position closer to the second end of the first sleeve than to the first end of the first sleeve,
   wherein the extension device is adjustable between a first configuration wherein the locking member is compressed such that a first portion of the through bore has a first diameter, and a second configuration wherein the locking member is expanded such that the first portion of the through bore has a diameter that is greater than the first diameter;
   wherein a distal end of the second sleeve remains entirely inside the first sleeve in the first configuration.

2. The extension device of claim 1, wherein the locking member is configured to inhibit attachment of a decoupling instrument to the extension device when the locking member is in the first configuration.

3. The extension device of claim 1, wherein the locking member comprises a spring that is compressible and/or extendible in a radial direction relative to the first sleeve axis.

4. The extension device of claim 1, wherein the locking member is positionable at least partially inside the second sleeve and comprises a collet positionable at least partially inside the first sleeve.

5. The extension device of claim 1, wherein the second sleeve is configured to be connected to the first sleeve through a coupling member that is configured to advance together with the second sleeve in an axial direction relative to the first sleeve.

6. The extension device of claim 5, wherein the coupling member comprises a bushing that is configured to be coupled to the first sleeve by an advancement structure that permits the coupling member to advance with the second sleeve relative to the first sleeve.

7. The extension device of claim 6, wherein the advancement structure comprises threads on the bushing and on the first sleeve.

8. The extension device of claim 7, wherein the locking member and the coupling member are formed as a single monolithic part.

9. The extension device of claim 5, wherein the coupling member is configured to be coupled to the second sleeve such that the coupling member can rotate with respect to the second sleeve.

10. The extension device of claim 5, wherein the locking member and the coupling member are formed as a single monolithic part.

11. The extension device of claim 1, further comprising a third sleeve that is selectively connectable to the first sleeve to enlarge an axial length of the extension device and wherein the third sleeve has an inner wall defining a passage sized for insertion of a portion of the first sleeve.

12. The extension device of claim 11, a pusher and wherein when the portion of the first sleeve is in the third sleeve, the pusher is adjustable between a first position wherein the pusher protrudes into the passage to clamp the first sleeve in the passage, and a second position wherein the pusher is positioned entirely outside of the passage for removing the first sleeve from the passage.

13. The extension device of claim 12, wherein the third sleeve has two opposite slots for the pusher to extend through, and wherein the pusher has an inner hollow section for the portion of the first sleeve to pass therethrough.

14. The extension device of claim 1, wherein, when the extension device is adjusted from the second configuration to the first configuration, there is movement of the first sleeve and the locking member relative to each other along a tapered surface at an engagement between the first sleeve and the locking member.

15. The extension device of claim 14, wherein the tapered surface is on the locking member and the tapering narrows in a direction from the second end of the first sleeve to the first end of the first sleeve.

16. An extension device system comprising:
a bone anchor comprising:
an anchoring section for anchoring to a bone; and
a receiving part connected to or configured to be connected to the anchoring section, the receiving part comprising two legs defining a channel for receiving a rod; and
an extension device for the bone anchor, comprising:
a first sleeve configured to be coupled to the receiving part;
a second sleeve positionable at least partially in and movable relative to the first sleeve, wherein the second sleeve is configured to be coupled to the receiving part; and
a locking member with a through bore, wherein the locking member is configured to be connected to the first sleeve and the second sleeve for moving the second sleeve axially relative to the first sleeve;
wherein when the first sleeve is coupled to the receiving part, the extension device is adjustable between a first configuration wherein the second sleeve is axially spaced apart from the receiving part and the through bore of the locking member has a first minimum diameter, and a second configuration wherein the second sleeve contacts the receiving part and the locking member is radially compressed such that the through bore of the locking member has a diameter smaller than the first minimum diameter.

17. The extension device system of claim 16, wherein each of the first sleeve and the second sleeve is configured to be coupled to the receiving part via a form-fit engagement.

18. The extension device system of claim 16, wherein the first sleeve is configured to be coupled to the receiving part via a form-fit engagement, and wherein the second sleeve is configured to be coupled to the receiving part via a frictional engagement.

19. The extension device system of claim 16, further comprising a second bone anchor and a second extension device.

20. The extension device system of claim 16, wherein in the second configuration, the locking member permits decoupling of one of the first sleeve or the second sleeve from the receiving part when the other one of the first sleeve or the second sleeve is decoupled from the receiving part.

21. The extension device system of claim 16, wherein the locking member inhibits decoupling of the first sleeve when the second sleeve is coupled to the receiving part.

22. The extension device system of claim 16, wherein in the first configuration, an abutment between the first sleeve and the receiving part restricts axial movement of the first sleeve relative to the receiving part.

23. The extension device system of claim 16, further comprising a third sleeve that is selectively connectable to the first sleeve to enlarge an axial length of the extension device and wherein the third sleeve has an inner wall defining a passage sized for insertion of a portion of the first sleeve.

24. The extension device system of claim 23, wherein the third sleeve has a pusher and wherein when the portion of the first sleeve is in the third sleeve, the pusher is adjustable between a first position wherein the pusher protrudes into the passage to clamp the first sleeve in the passage, and a second position wherein the pusher is positioned entirely outside of the passage for removing the first sleeve from the passage.

25. The extension device system of claim 24, wherein the third sleeve has two opposite slots for the pusher to extend through, and wherein the pusher has an inner hollow section for the portion of the first sleeve to pass therethrough.

26. A method of decoupling an extension device from a bone anchor, the bone anchor comprising an anchoring section for anchoring to a bone and a receiving part connected to the anchoring section, the receiving part comprising two legs defining a channel for receiving a rod, the extension device comprising a first sleeve configured to be coupled to the receiving part, a second sleeve positionable at least partially in and movable relative to the first sleeve, wherein the second sleeve is configured to be coupled to the receiving part, and a locking member with a through bore, wherein the locking member is configured to be connected to the first sleeve and the second sleeve for moving the second sleeve axially relative to the first sleeve, wherein when the first sleeve is coupled to the receiving part, the extension device is adjustable between a first configuration wherein the second sleeve is axially spaced apart from the receiving part and the through bore of the locking member has a first minimum diameter, and a second configuration wherein the second sleeve contacts the receiving part and the locking member is radially compressed such that the through bore of the locking member has a diameter smaller than the first minimum diameter, the method comprising:

axially advancing the second sleeve towards the receiving part when the second sleeve is in the first sleeve, the first sleeve is attached to the receiving part and connected to the locking member, and when the through bore of the locking member has the first minimum diameter; and contacting the receiving part with the second sleeve such that the through bore of the locking member has the diameter smaller than the first minimum diameter.

* * * * *

UNITED STATES PATENT AND TRADEMARK OFFICE
CERTIFICATE OF CORRECTION

PATENT NO. : 9,956,012 B2
APPLICATION NO. : 14/740228
DATED : May 1, 2018
INVENTOR(S) : Timo Biedermann et al.

Page 1 of 1

It is certified that error appears in the above-identified patent and that said Letters Patent is hereby corrected as shown below:

In the Claims

Column 15, Line 33, Claim 12, after "11," insert -- wherein the third sleeve has --

Signed and Sealed this
Second Day of July, 2019

Andrei Iancu
*Director of the United States Patent and Trademark Office*